US006180388B1

(12) United States Patent
Crouzet et al.

(10) Patent No.: US 6,180,388 B1
(45) Date of Patent: Jan. 30, 2001

(54) ENZYMES AND MICRO ORGANISMS WITH AMIDASE ACTIVITY WHICH HYDROLYZE POLYAMIDES

(75) Inventors: Joël Crouzet, Sceaux; Didier Faucher, Paris; Olivier Favre-Bulle, Lyon; Catherine Jourdat, Lyon; Dominique Petre, Lyon; Jérôme Pierrard, Lyon; Denis Thibaut, Paris; Carole Guitton, Lyon, all of (FR)

(73) Assignee: Rhone-Poulenc Fibres et Polymeres S.A., Courbevoie Cedex (FR)

( * ) Notice: Under 35 U.S.C. 154(b), the term of this patent shall be extended for 0 days.

(21) Appl. No.: 09/000,040

(22) PCT Filed: Jul. 17, 1996

(86) PCT No.: PCT/FR96/01118

§ 371 Date: Apr. 3, 1998

§ 102(e) Date: Apr. 3, 1998

(87) PCT Pub. No.: WO97/04083

PCT Pub. Date: Feb. 6, 1997

(30) Foreign Application Priority Data

Jul. 18, 1995 (FR) .................................................. 95/08917

(51) Int. Cl.[7] .............................. C12N 9/80; C12N 15/55; C12N 15/70; D06M 16/00
(52) U.S. Cl. ..................... 435/228; 435/263; 435/252.3; 435/252.33; 435/320.1; 536/23.2
(58) Field of Search ..................................... 435/263, 264, 435/228, 69.1, 252.3, 252.33, 320.1; 536/23.2

(56) References Cited

U.S. PATENT DOCUMENTS 5,468,632 * 11/1995 Cantwell et al. ..................... 435/197

5,629,190 * 5/1997 Petre et al. ............................ 435/227

FOREIGN PATENT DOCUMENTS 2 700 777   7/1994 (FR) .

OTHER PUBLICATIONS

Okada, H., et al., Nature, vol. 306, "Evolutionary adaptation of plasmid–encoded enzymes for degrading nylon oligomers", pp. 203–206, 1983.*

Negoro, S., et al., European Journal of Biochemistry, vol. 185, "Determination of the active–site serine of 6–aminohexanoate–dimer hydrolase", pp. 521–524, 1989.*

(List continued on next page.)

*Primary Examiner*—Ponnathapu Achutamurthy
*Assistant Examiner*—William W. Moore
(74) *Attorney, Agent, or Firm*—Burns, Doane, Swecker & Mathis, L.L.P.

(57) ABSTRACT

The present invention relates to a process for the enzymatic hydrolysis of polyamides 6.6 to give adipic acid monomers and hexamethylenediamine monomers. The present invention further relates to an enzyme with amidase activity particularly towards substrates of the oligomer type derived from PA 6.6 and/or PA 6, said enzyme being characterized in that it consists of a peptide sequence corresponding to SEQ ID NO: 1 in the attached sequence listing and/or at least one polypeptide homologous to this sequence. The invention further relates to the DNA coding for said enzyme and to the biological precursors thereof The invention further relates to the microorganisms capable of producing this enzyme and to the hydrolysis process in which this enzyme and/or these microorganisms are applied.

20 Claims, 2 Drawing Sheets

OTHER PUBLICATIONS

Hatanaka, H. S., et al., Journal of Fermentation and Bioengineering, vol. 71, "Alteration of catalytic function of 6–aminohexanoate–dimer hydrolase by site–diredted mutagenesis", pp. 191–193, 1991.*

Kato, K., et al., European Journal of Biochemistry, vol. 200, "Amino acid alterations essential for increasing the catalytic activity of the nylon–oligomer–degradation enzyme of Flavobacterium sp.", pp. 165–169, 1991.*

Prijambada, I. D., et al., Applied and Environmental Microbiology, vol. 61, "Emergence of nylon oligomer degradation enzymes in Pseudomonas aeruginosa PAO through experimental evolution", pp. 2020–2022, 1995.*

J. Gen. Microbiol., vol. 139, 1993, pp. 878–895, XP000608206, Kanagawa et al, "Characterization of 6–aminohexanoate–dimer hydrolase from Pseudomonas sp. NK87" & Database Strand Embl.: Empro:Ps6ahdh, AC = D10678, 5.

Appl. Environ. Microbiol., vol. 59, No. 11, Nov. 1993, pp. 3978–3980, XP000566953, Kakudo et al, "Nylon oligomer degradation gene, nylC, om plasmid pOAD2 from Flavobacterium strain encodes endo–type 6–aminohexanoate oligomer hydrolase : purification and characterization of the nylC gene product".

J. Bacteriology, vol. 174, No. 24, 1992, pp. 7948–7953, XP000566945, Negoro et al,: "A new nylon oligomer degradation gene (nylC) on plasmid pOAD2 from a Flavobacerium sp.".

Biodegradation, vol. 5, No. 3–4, Dec. 1994, pp. 185–194, XP000567371, Negoro et al, "The Nylon Oligomer Biodegradation System of Flavobacterium and Pseudomonas".

* cited by examiner

SEQUENCE LISTING

<160> NUMBER OF SEQ ID NOS: 4

<210> SEQ ID NO 1
<211> LENGTH: 421
<212> TYPE: PRT
<213> ORGANISM: Comamonas acidovorans

<400> SEQUENCE: 1

```
Met Asn Arg Thr Tyr His Arg Arg Asp Val Leu Arg Ile Leu Gly Val
1               5                   10                  15

Gly Thr Ala Leu Gly Gly Ala Ala Leu Leu Gly Ala Cys Gly Gly Ser
            20                  25                  30

Gly Gly Asn Glu Ala Pro Arg Glu Gln Ile Ala Ser Ser Leu Phe Ser
        35                  40                  45

Thr Thr Pro Glu Asn Arg Ala Ala Thr Phe Arg Asn Ala Asp Arg Ile
    50                  55                  60

Val Tyr Ser Arg Thr Ile Lys Arg Gly Ala Thr Thr Met Pro Leu Lys
65                  70                  75                  80
```

```
Pro His His Val Ser Leu Ala Ser Leu Thr Tyr Asp Tyr Ala Gly Lys
                 85                  90                  95

Thr Thr Asn Val Asp Asp Tyr Met Gln Arg Asn Arg Thr Ala Gly Leu
            100                 105                 110

Leu Ile Leu Lys Gly Gly Ala Val Ala Leu Glu Arg Tyr Gly Met Gly
        115                 120                 125

Asn Thr Glu Thr Ser Arg Trp Thr Ser Trp Ser Val Ala Lys Ser Val
    130                 135                 140

Thr Ser Thr Leu Val Gly Ala Ala Leu Lys Asp Gly His Ile Ala Ser
145                 150                 155                 160

Leu Asp Asp Pro Val Thr Arg Tyr Val Thr Ala Leu Lys Gly Ser Ala
                165                 170                 175

Tyr Glu Gln Asn Thr Ile Arg Glu Leu Leu Arg Met Thr Ser Gly Val
            180                 185                 190

Arg Trp Ile Glu Ala Tyr Ser Glu Thr Gly Asn Ser Asp Ile Ala Arg
        195                 200                 205

Leu Arg Glu Ala Tyr Ser Ser Gly Lys Ser Gly Ser Val Met Glu Leu
    210                 215                 220

Met Arg Thr Arg Pro Arg Ala Ala Pro Gly Ser Val Phe Asn Tyr
225                 230                 235                 240

Ser Thr Gly Glu Ser Tyr Val Leu Gly Ala Val Val Ala Ala Ala Thr
                245                 250                 255

Gly Thr Thr Leu Ser Asp Tyr Phe Ser Arg Lys Val Trp Ala Pro Phe
            260                 265                 270

Gly Met Glu Ala Asp Gly Tyr Trp Gln Leu Asp Ser Glu Gly Gly Leu
        275                 280                 285

Glu Met Gly Gly Ala Asn Phe Ser Ala Thr Leu Arg Asp Tyr Gly Arg
    290                 295                 300

Phe Gly Leu Phe Phe Ser Arg Glu Gly Val Val Asn Gly Thr Ala Val
305                 310                 315                 320

Leu Pro Leu Gly Trp Arg Ala Leu Ala Ser His Pro Asp Ser Pro Val
                325                 330                 335

Thr Asn Tyr Gly Ala Leu Tyr Lys Asp Tyr Pro Leu Gly Tyr Gly Tyr
            340                 345                 350

Gln Trp Trp Ala Leu Pro Gly Lys Asp Thr Thr Ile Pro Ala Gln Asp
        355                 360                 365

Arg Pro Phe Thr Ala Gln Gly Ile Tyr Gly Gln Phe Ile Tyr Ile Asp
    370                 375                 380

Pro Lys Glu Asp Val Val Ala Val Val Trp Ser Ala Trp Asn Asn Ser
385                 390                 395                 400

Trp Val Asp Ser Ala Glu Phe Glu Thr Phe Ala Leu Leu Ser Lys Ala
                405                 410                 415

Val Glu Met Leu Lys
            420

<210> SEQ ID NO 2
<211> LENGTH: 1263
<212> TYPE: DNA
<213> ORGANISM: Comamonas acidovorans

<400> SEQUENCE: 2
atgaacagga cataccaccg tcgcgatgtg ctgagaattt tgggtgttgg aactgcactt      60
ggaggcgcgg cgcttctcgg cgcctgtggc ggcagtggag caacgaagc gcctcgggaa     120 caaattgcat cgagcctatt cagcacaact cccgaaaacc gggcggcaac tttccggaat    180
```

```
gccgaccgaa ttgtttactc acgcaccatc aagcgtggcg ccacgaccat gcctctgaag      240
ccgcaccatg tctcgctggc gtccctcaca tatgactatg cggggaaaac cactaacgtg      300
gatgactaca tgcagcgcaa tcgcacagct ggattgctta tcttgaaagg cggagcagtc      360
gcgctggagc gctatggcat gggcaacacc gaaacgtccc ggtggacttc atggtcagtc      420
gccaaatctg tcacctccac cttggttggc gcagcgctga aggatgggca cattgccagc      480
ctagacgacc ctgtgacgag gtatgtgacg gctttaaaag gcagcgcgta tgaacagaac      540
acaatacgtg agctgctacg gatgacttcc ggcgtacgtt ggattgaagc ctacagcgag      600
acgggcaact ccgacattgc ccgactgaga gaggcgtata gttccgggaa agcggcagc      660 gtgatggagc tgatgcgcac acgcccgcgt gcggcagccc tggcagtgt gtttaactac      720 agcacagggg agagttacgt gctaggcgca gtagttgcag cggccactgg cacaactttg      780
agtgattatt tctcccggaa agtatgggca ccgttcggca tggaggccga tggctattgg      840
cagctggatt ccgaaggagg actggaaatg ggggcgcaa atttcagcgc gaccttgcga      900
gactacggga ggttcggctt gttcttctcg cgcgaaggcg tcgtcaatgg cactgctgtt      960
ctgccgcttg ggtggcgggc tcttgctagc catcccgatt cgccagtaac caactacgga     1020
gctctttaca aagactaccc gcttggctat ggataccaat ggtgggcact cccgggcaaa     1080
gatacaacaa ttccagctca agaccgcccc ttcaccgctc aaggcatcta cggtcagttc     1140
atttacatcg atcccaagga ggatgttgtt ccgtagtgt ggagtgcgtg aacaactca      1200 tgggtcgaca gcgccgagtt tgaaacgttt gcacttctct cgaaggccgt agaaatgttg     1260
aaa                                                                    1263

<210> SEQ ID NO 3
<211> LENGTH: 355
<212> TYPE: PRT
<213> ORGANISM: Comamonas acidovorans

<400> SEQUENCE: 3

Met Asn Thr Thr Pro Val His Ala Leu Thr Asp Ile Asp Gly Gly Ile
  1               5                  10                  15

Ala Val Asp Pro Ala Pro Arg Leu Ala Gly Pro Pro Val Phe Gly Gly
                 20                  25                  30

Pro Gly Asn Asp Ala Phe Asp Leu Ala Pro Val Arg Ser Thr Gly Arg
             35                  40                  45

Glu Met Leu Arg Phe Asp Phe Pro Gly Val Ser Ile Gly Ala Ala His
     50                  55                  60

Tyr Glu Glu Gly Pro Thr Gly Ala Thr Val Ile His Ile Pro Ala Gly
 65                  70                  75                  80

Ala Arg Thr Ala Val Asp Ala Arg Gly Gly Ala Val Gly Leu Ser Gly
                 85                  90                  95

Gly Tyr Asp Phe Asn His Ala Ile Cys Leu Ala Gly Ala Cys Tyr
            100                 105                 110

Gly Leu Glu Ala Gly Ala Gly Val Ser Asp Ala Leu Leu Glu Arg Leu
        115                 120                 125

Glu His Arg Thr Gly Phe Ala Glu Leu Gln Leu Val Ser Ser Ala Val
    130                 135                 140

Ile Tyr Asp Phe Ser Ala Arg Ser Thr Ala Val Tyr Pro Asp Lys Ala
145                 150                 155                 160

Leu Gly Arg Ala Ala Leu Glu Phe Ala Val Pro Gly Glu Phe Pro Gln
                165                 170                 175
```

```
Gly Arg Ala Gly Ala Gly Met Ser Ala Ser Ala Gly Lys Val Asp Trp
            180                 185                 190

Asp Arg Thr Glu Ile Thr Gly Gln Gly Ala Ala Phe Arg Arg Leu Gly
            195                 200             205

Asp Val Arg Ile Leu Ala Val Val Pro Asn Pro Val Gly Val Ile
            210                 215             220

Val Asp Arg Ala Gly Thr Val Val Arg Gly Asn Tyr Asp Ala Gln Thr
225                 230                 235                 240

Gly Val Arg Arg His Pro Val Phe Asp Tyr Gln Glu Ala Phe Ala Glu
                245                 250                 255

Gln Val Pro Pro Val Thr Glu Ala Gly Asn Thr Thr Ile Ser Ala Ile
            260                 265                 270

Val Thr Asn Val Arg Met Ser Pro Val Glu Leu Asn Gln Phe Ala Lys
            275                 280                 285

Gln Val His Ser Ser Met His Arg Gly Ile Gln Pro Phe His Thr Asp
            290                 295                 300

Met Asp Gly Asp Thr Leu Phe Ala Val Thr Thr Asp Glu Ile Asp Leu
305                 310                 315                 320

Pro Thr Thr Pro Gly Ser Ser Arg Gly Arg Leu Ser Val Asn Ala Thr
                325                 330                 335

Ala Leu Gly Ala Ile Ala Ser Glu Val Met Trp Asp Ala Val Leu Glu
            340                 345                 350

Ala Gly Lys
    355

<210> SEQ ID NO 4
<211> LENGTH: 1068
<212> TYPE: DNA
<213> ORGANISM: Comamonas acidovorans

<400> SEQUENCE: 4
atgaatacga caccggtcca cgcactcacc gacatcgacg gcgggatcgc cgtcgatccc    60
gcaccccggc tggccggccc tccggtcttc ggggtccgg gcaacgacgc cttcgatctc    120
gcgccggtca ggagcacggg ccgcgagatg ctgcggttcg acttccccgg ggtcagcatc    180
ggcgcggcgc actacgagga ggggcccacc ggtgcgaccg tgatccacat ccccgccggc    240
gcccgcaccg cggtggacgc gcggggcggg gcggtggggc tctccggcgg ctacgacttc    300
aaccacgcca tctgcctggc cggcggagcc tgctacgggc tcgaggcggg cgccggggtg    360
agcgacgcgc tcctggaacg cctcgagcat cgcaccggct cgccgagct ccagctggtg    420 tcgtcggcg tcatctacga cttctcggcg cgctccaccg cggtctaccc cgacaaggcg    480
ctcggccgcg cggcgctcga attcgccgtt cccggtgagt tcccgcaggg gcgggcgggc    540
gcgggcatga gcgcgtccgc gggcaaggtg gactgggacc gcaccgagat caccgggcag    600
ggcgcggcgt tccgtcgtct cggcgacgtg cgcatcctcg ccgtcgtcgt gccgaacccg    660
gtcggtgtga tcgtggaccg cgcgggcacg gtggtgcgcg caactacga cgcgcagacc    720 ggggtccggc gccacccggt gttcgactac caggaggcgt tcgccgagca ggtcccgccc    780
gtcaccgagg ccggcaacac cacgatcagc gcgatcgtca cgaacgtgcg gatgagcccc    840
```

```
gtcgagctga accagttcgc caagcaggtg cacagttcga tgcaccgcgg catccagccg      900
ttccacaccg acatggacgg cgacacgctc ttcgccgtca ccaccgacga gatcgatctg      960
ccgacgaccc cggggtcgtc gcgcgggcgg ctgtcggtga acgcgaccgc gctcggcgcg     1020
atcgcctccg aggtgatgtg ggacgccgtc ctcgaggccg gcaagtag                  1068
```

ENZYMES AND MICRO ORGANISMS WITH AMIDASE ACTIVITY WHICH HYDROLYZE POLYAMIDES

TECHNICAL FIELD

The present invention relates in general terms to the enzymatic hydrolysis of amides, especially secondary amides.

More precisely, the invention relates first of all to a process for the enzymatic hydrolysis of substrates of the polyamide 6.6 type to give the two comonomers, A and B, of said substrates. The invention further relates to enzymes and/or microorganisms which are capable of being used in the enzymatic hydrolysis of amide groups, preferably on substrates containing at least one amide group, for example polyamides (PA). The invention further relates to the genetic tools expressing these enzymes.

PRIOR ART

In this field, SMITH R. et al. are the authors of an article published in "Journal of Biomedical Materials Research (1987), vol. 21, p. 991–1003" and disclose the bringing of samples of polyamide 66 labeled with carbon 14 into contact with enzymes of the papain, trypsin and α-chymotrypsin type. These known polypeptides degrade polyamide 66 slightly, but the hydrolysis is not sufficiently significant to be able to be exploited on the industrial scale.

It is also known, through the article by KINOSHITA et al. (Eur. J. Biochem. 116, 547–551, 1981), that Flavobacterium sp KI 72 is able to produce a first enzyme ($E_1$) which catalyzes the hydrolysis of cyclic dimers of 6-aminohexanoic acid to linear dimers of this same acid, and a second enzyme ($E_2$) which is capable of converting this linear dimer to two molecules of 6-aminohexanoic acid or aminocaproic acid. The enzymatic pathway in question is summarized below.

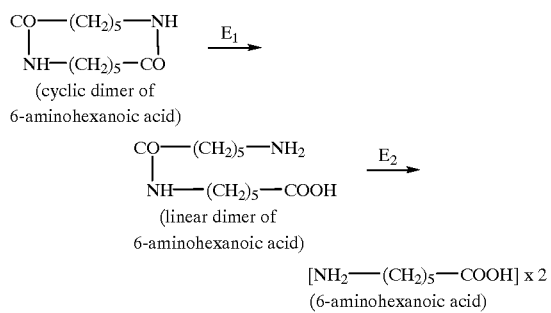

The activity of the linear amidase $E_2$ is optimal for the dimers and decreases as the degree of polymerization increases, no longer being significant beyond oligomers with a degree of polymerization ($DP_n$) of 7.

An enzyme $E_3$ active towards cyclic and linear oligomers of 6-aminohexanoic acid of $DP_n \geq 3$ (PA 6) is also known. $E_3$ is described by NEGORO et al. in "Journal of Bacteriology, Dec. 1992, vol. 174, no. 24, p. 7948–7953". $E_3$ also originates from Flavobacterium sp KI 72.

In their article published in "Journal of Bacteriology, June 1989, p. 3187–3191, vol. 171 no. 6", TSUCHIYA et al. teach that a high degree of homology exists between the enzymes $E_1$ from Flavobacterium sp KI 72 and one of the enzymes derived from Pseudomonas sp NK 87. These enzymes $E_1$ and homologs, and the enzymes $E_2$, more particularly the latter, are said to be active on oligomers or polyamides (PA 6) of the formula

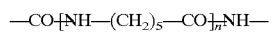

where: $2 \leq n \leq 20$.

The disadvantage of these enzymes derived from Flavobacterium or Pseudomonas is that they have relatively low specific activities towards oligomers, said activities amounting to at most only 1.05 micromol of aminocaproic acid produced per minute and per milligram of protein from a substrate consisting of a trimer. Furthermore, these enzymes are specific for homo-oligomers.

It is thus apparent that the prior art does not comprise means for the enzymatic hydrolysis of amide groups which have a high performance, are viable and can be applied to amides, including especially secondary amides, of a variety of types, particularly of the co-oligomer and/or homo-oligomer type.

DISCLOSURE OF THE INVENTION

Therefore, after lengthy and laborious research, the Applicant succeeded in isolating and characterizing a novel enzyme of the amidase type formed by one or more polypeptides which, in particular, can be derived from novel microorganisms isolated from the biotype and/or novel recombinant microorganisms obtained from these natural microorganisms.

Consequently, the present invention relates firstly to an enzymatic hydrolysis process and secondly to an enzyme.

The process according to the invention for the hydrolysis of (poly)amides characterized in that:

enzymatic hydrolysis is carried out on substrates comprising (poly)amides of the following formula (I):

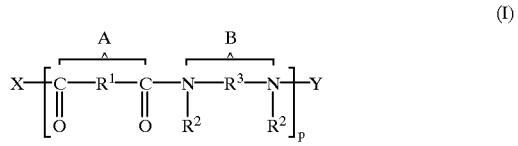

in which:

A and B are monomer units, $R^1$ and $R^3$ are identical or different—preferably different—divalent radicals representing a substituted or unsubstituted, linear or branched (cyclo)alkylene, an arylene or an arylalkylene, the aromatic radicals optionally being polycondensates and the number of carbons in the alkylenes being greater than or equal to 4, preferably between 4 and 12, $R^2$ corresponds to identical or different—preferably identical—radicals selected from hydrogen and/or alkyl radicals advantageously having from 1 to 6 carbons, X is:
either $X^1$=OH, OM or $OR^4$, where M is selected from metals, preferably alkali metals and alkaline earth metals, and $R^4$ is a linear or branched alkyl containing from 1 to 6 carbon atoms, or $X^2 =$

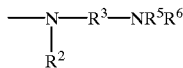

where $R^2$ and $R^3$ are as defined above and $R^5$ and $R^6$, which are identical or different, have the same definition as that given above for $R^2$, Y is:
either $Y^1$=hydrogen,
or $Y^2 =$

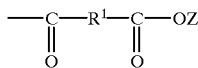

where $R^1$ is as defined above and Z is hydrogen, $M^1$ defined in the same way as M, or $R^4$,
with the following conditions:
-a- if $X=X^1$, then $Y=Y^1$ or $Y^2$,
-b- if $X=X^2$, then $Y=Y^2$,
and, finally, p is between 1 and 4, preferably between 1 and 3; and it is capable of converting the above-mentioned substrates (I) to monomers A, on the one hand, and monomers B, on the other.

The present invention further relates to a family of enzymes of the amidase type which are capable (inter alia) of being used in the process defined above.

The enzyme belonging to the family according to the invention is an amidase characterized in that:
-⑤ →it is active, especially towards substrates of the (poly)amide type having the following formula:

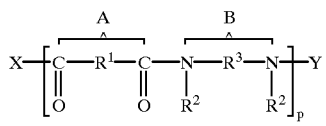

in which:

A and B are monomer units, $R^1$ and $R^3$ are identical or different—preferably different—divalent radicals representing a substituted or unsubstituted, linear or branched (cyclo)alkylene, an arylene or an arylalkylene, the aromatic radicals optionally being polycondensates and the number of carbons in the alkylenes being greater than or equal to 4, preferably between 4 and 12, $R^2$ corresponds to identical or different—preferably identical—radicals selected from hydrogen and/or alkyl radicals advantageously having from 1 to 6 carbons, X is:
either $X^1$=OH, OM or $OR^4$, where M is selected from metals, preferably alkali metals and alkaline earth metals, and $R^4$ is a linear or branched alkyl containing from 1 to 6 carbon atoms, or $X^2 =$

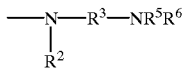

where $R^2$ and $R^3$ are as defined above and $R^5$ and $R^6$, which are identical or different, have the same definition as that given above for $R^2$, Y is:
either $Y^1$=hydrogen,
or $Y^2 =$

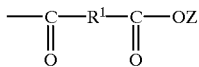

where $R^1$ is as defined above and Z is hydrogen, $M^1$ defined in the same way as M, or $R^4$, with the following conditions:
-a- if $X=X^1$, then $Y=Y^1$ or $Y^2$,
-b- if $X=X^2$, then $Y=Y^2$,
and, finally, p is between 1 and 4, preferably between 1 and 3;

-② →and it is capable of converting the above-mentioned substrates (I) to monomers A, on the one hand, and monomers B, on the other.

Among this family of enzymes according to the invention, it is advantageous to isolate an enzyme with amidase activity which comprises the peptide sequence as shown in the attached sequence SEQ ID NO : 1, or a homologous peptide sequence having a homology of at least 80%, preferably at least 90% and particularly preferably at least 95% with SEQ ID NO: 1.

According to one advantageous characteristic of the invention, this enzyme has amidase activity particularly towards substrates of the (poly)amide type having the following formula (II):

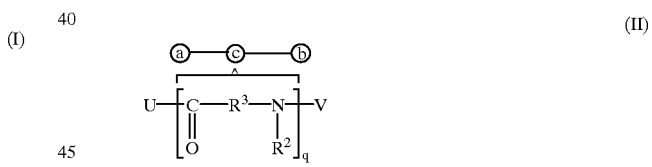

in which:

$R^2$ and $R^3$ are as defined above,

U and V respectively have the same definitions as those given above for $X^1$ and $Y^1$ in formula (1) given in claim 1, and q=1 to 8.

The invention initially arose from the isolation of a wild-type strain which produced the enzyme, namely: *Comamonas acidovorans* N 12.

The identification of this wild-type strain is the result of a long-winded screening operation. This identification was effected on the basis of the morphological, cultural, biochemical and antigenic properties which could be determined by reference to the official international criteria of microbiological taxonomy.

The Applicant's merit is not limited to the isolation of this wild-type strain, but also extends to the isolation of the amidase defined above. The microorganism *Comamonas acidovorans* N 12 is not the exclusive biological precursor of this amidase. In fact, it is also necessary to consider all recombinant microorganisms and wild-type strains which have a similar enzymatic activity.

The recombinant microorganisms are those which possess in their genome a DNA sequence coding for the amidase considered in the present invention.

According to another of its aspects, the invention further relates to an enzymatic hydrolysis process in which the above-mentioned enzyme and/or the above-mentioned wild-type microorganism and/or at least one of its above-mentioned recombinant microorganisms are used.

According to the invention, the enzyme substrates and/or their biological precursors (microorganisms/recombinant microorganisms) are polyamides and, more precisely, oligomers whose repeat polymerization group is a secondary amide group —CO—NH—.

These oligomers have repeat units of formulae (I) and/or (II). The repeat units (I) are advantageously formed of two monomer units, A and B, which are respectively dicarbonyl and diamine units and are joined together by a secondary amine group.

In one preferred modality of the invention:
the monomer A is a residue

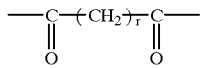

where r is between 4 and 12 and is preferably equal to 4, and the monomer B is a residue

where s is between 4 and 12 and is preferably equal to 6.

Thus, for the substrates (I), a preferred example of a dimer is that formed by

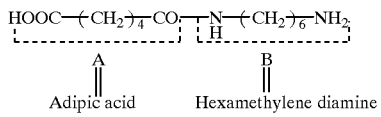

The corresponding polyamide is PA 6.6.

The repeat units (II), on the other hand, are preferably formed by monomer units denoted as (a)—(c)—(b), in which c is a skeleton of the amino acid type whose end groups (a) and (b) are carboxyl and amino groups respectively.

A typical example of (a)—(c)—(b) is a derivative of c-aminocaproic acid, the monomer of polyamide 6 (PA 6).

The following may be mentioned among the oligomers of the polyamide type which are suitable for the invention:

the polyamide oligomers obtained by the polycondensation of saturated aliphatic carboxylic diacids having from 6 to 12 carbon atoms with saturated aliphatic primary diamines having from 6 to 12 carbon atoms, the polyamino acid oligomers obtained either by the direct homopolycondensation of an ω-aminoalkanoic acid containing a hydrocarbon chain having from 4 to 12 carbon atoms, or by the hydrolytic opening and polymerization of the lactams derived from these acids, the copolyamide oligomers obtained from the starting monomers of the above-mentioned polyamides, it also being possible for the acid component of these copolyamides to consist partly of an aromatic acid such as terephthalic acid and/or isophthalic acid, and mixtures of these polyamide oligomers.

The following may be mentioned as illustrative examples of the polyamides obtained by the polycondensation of diacids and diamines:

polyamide 4,6 (polymer of tetramethylenediamine and adipic acid), polyamide 6,6 (polymer of hexamethylenediamine and adipic acid) (PA 6.6), polyamide 6,9 (polymer of hexamethylenediamine and azelaic acid), polyamide 6,10 (polymer of hexamethylenediamine and sebacic acid), polyamide 6,12 (polymer of hexamethylenediamine and dodecanedioic acid).

The following may be mentioned as illustrations of suitable polyamino acids:

polyamide 4 (polymer of 4-aminobutanoic acid or γ-butyrolactam), polyamide 5 (polymer of 5-aminopentanoic acid or δ-amylolactam), polyamide 6 (polymer of ε-caprolactam), polyamide 7 (polymer of 7-aminoheptanoic acid), polyamide 8 (polymer of capryllactam), polyamide 9 (polymer of 9-aminononanoic acid), polyamide 10 (polymer of 10-aminodecanoic acid), polyamide 11 (polymer of 11-aminoundecanoic acid), polyamide 12 (polymer of 12-aminododecanoic acid or laurolactam).

The following may be mentioned as illustrative examples of copolyamides:

polyamide 6,6/6,10 (copolymer of hexamethylenediamine, adipic acid and sebacic acid), polyamide 6,6/6 (copolymer of hexamethylenediamine, adipic acid and caprolactam).

Without implying a limitation, the preferred substrates according to the invention are polyamide oligomers obtained by the polycondensation of diacids A and diamines B, particularly oligomers of PA 6.6.

The number of monomers A and B, on the one hand, or (a)—(c)—(b), on the other, in the substrates (I) and (II) according to the invention is advantageously between 2 and 8, preferably between 2 and 6.

It should be pointed out that this number of monomers A and B in the oligomer or polymer molecules will also be called $DP_n$ in the present disclosure.

Characteristic substrates (I) are e.g. advantageously water-soluble oligomers such as AB, ABA and ABAB.

It should be pointed out that this number of monomers A and B in the oligomer or polymer molecules will also be called $DP_n$ in the present disclosure.

These particular substrates are among the substrates (I) and (II) which can be hydrolyzed by the enzyme of the invention and/or its biological precursors because they possess at least one carboxyl end group.

When the enzymatic substrates are oligomers containing monomers A and B, the final hydrolysis products can be monomers A and B.

When the substrates are oligomers (II) (monomers ((a)—(c)—(b)), the final hydrolysis products can be monomers (a)—(c)—(b).

The enzyme according to the invention can also be characterized through its activity and/or its affinity towards some of the above-mentioned substrates.

Thus, according to a first advantageous characteristic, the amidase in question is:

firstly active towards a substrate (I) formed by a tetramer of A and B ($DP_n=4$, i.e. p=2, $X=X^1$ and $Y=Y^1$), and secondly capable of converting this substrate on the one hand to an oligomer of $DP_n=3$ and on the other hand to a monomer A with a specific enzymatic activity ($U_s$)—expressed in µmol of hydrolyzed ABAB×h$^{-1}$× mg$^{-1}$ of protein and measured under given conditions—which is greater than or equal to 1000.

A second advantageous characteristic of this amidase is that it is active towards a substrate (I) formed by a trimer ABA, and capable of converting this trimer to a monomer A and a dimer AB with a specific enzymatic activity greater than or equal to 1000 µmol of hydrolyzed substrate×h$^{-1}$× mg$^{-1}$ of protein.

A third advantageous characteristic of this amidase is that it is active towards a substrate (I) formed by a dimer of the type AB, and capable of converting this dimer to two monomers A and B with a specific enzymatic activity greater than 1500 µmol of hydrolyzed substrate×h$^{-1}$×mg$^{-1}$ of protein.

The enzymatic activity of the pure amidase is measured under the following conditions: phosphate buffer, pH 6 to 8 and temperature=30° C.

The amidase enzyme of the invention has at least one of these three non-limiting characteristics.

As already indicated above, the use of the enzyme of the invention in the enzymatic hydrolysis of amides can consist in using only the enzyme per se instead of the biological precursors (wild-type or recombinant microorganisms) which produce said enzyme, or a mixture of both.

On the subject of enzyme producers, it should be emphasized that the enzyme forming the subject of the invention is also characterized in that it is produced by microorganisms of the type *Comamonas acidovorans* (N 12), preferably of the same type as the strain referenced and deposited in the Collection Nationale de Cultures de Micro-organismes—Institut Pasteur PARIS—under no. I 1522 on Jan. 4, 1995, and/or by the recombinant microorganisms as described above.

The present invention further relates to novel microorganisms capable of producing the amidase enzyme according to the invention, as defined above. By virtue of this ability, the particular characteristics of these microorganisms are, on the one hand, a capacity to hydrolyze the amide groups of a polyamide compound comprising at least one amide group, and particularly oligomers. More precisely, these microorganisms have a specific selectivity and hydrolytic activity towards the substrates (I) and (II) defined above. In the case of the substrates (I), the oligomers are for example the water-soluble oligomers mentioned above: ABAB and/or ABA and/or AB, inter alia.

More precisely, these microorganisms can preferably consist of *Comamonas acidovorans* mentioned above, preferably the strain referenced and deposited in the Collection Nationale de Cultures de Micro-organismes under no. I 1522 on Jan. 4, 1995, or recombinant microorganisms thereof, as described above.

Advantageously, the microorganisms according to the invention are capable of hydrolyzing at least one substrate formed by a polyamide oligomer and, more particularly, by a dimer AB, which is destined to be converted to two monomers A and B, the microorganisms being capable of performing the hydrolysis.

Apart from the biological precursors of the amidase in question, the present further relates to the genetic material under whose control it can be synthesized via recombinant or non-recombinant microorganisms. Consequently, the present invention relates to a DNA sequence coding for an enzyme with amidase activity, characterized in that it is selected from the following sequences:

Δ the DNA sequence as represented by SEQ ID NO: 2 in the attached sequence listing and coding for at least one enzyme with amidase activity, Δ an analog of this sequence which results from the degeneracy of the genetic code, and Δ a DNA sequence hybridizing with the above-mentioned sequence or with at least one fragment thereof and coding for an enzyme with amidase activity.

The enzymes resulting from the expression of the above-mentioned DNA sequence are also included in the field of the invention.

The wild-type microorganisms (e.g. I 1522) and the recombinant microorganisms isolated by the Applicant each contains at least one expression cassette comprising the DNA sequence SEQ ID NO: 2 referred to above, and optionally, upstream thereof, at least one promoter sequence and at least one ribosome binding site.

The present invention further relates to a process for the hydrolysis of substrates which are at least partly formed by the substrates (I) and/or (II) as defined above, characterized in that it consists in using at least one enzyme and/or at least one of the microorganisms as presented above.

It may be advantageous, according to the invention, to have several enzymes with complementary spectra. Therefore, one of the variants of the above-mentioned process can be to have the use of at least one other type of enzyme and/or at least one of its wild-type and/or recombinant biological precursors. In this variant, the substrates consist at least partly of oligomers whose $DP_n$ is less than 40, preferably 20 and particularly preferably 12, and which are derived from polyamides at least originating from polycondensation between diacid monomers (A) and diamine monomers (B).

The hydrolysis process according to this variant is characterized in that:

it produces oligomers with a degree of polymerization ($DP_n$) less than or equal to 3 and preferably produces monomers A and B, and the following are used:

at least one enzyme and/or at least one microorganism as defined above, and at least one other type of enzyme and/or to at least one of its wild-type and/or recombinant biological precursors, said enzyme being:

an enzyme $E_3$ produced under the control of the nyl-c gene of Flavobacterium sp KI 72, and/or an enzyme called PAM I as defined by the attached peptide sequence SEQ ID NO : 3, it being possible, inter alia, for such an enzyme to be produced by the microorganism referenced and deposited in the Collection Nationale de Cultures de Micro-organismes—Institut Pasteur PARIS—under no. I 1495 on Nov. 29, 1994.

Oligomers hydrolyzable by the above enzymes can be obtained by thermal and/or chemical (acid) lysis of the groups of the amide type.

Other advantageous modalities of the process according to the invention use especially biological precursors of the enzyme (or enzymes) and a culture medium comprising, for example:

a carbon source preferably comprising at least one compound containing at least one amide group, said carbon source optionally comprising a complement advantageously selected from carbohydrates, sucrose being particularly preferred, and optionally a compound capable of inducing enzyme production without being consumed by the biological precursors, said compound preferably being selected from amides.

The process according to the invention for the enzymatic hydrolysis of amides can have numerous applications, for example in organic synthesis for the manufacture of compounds from amide compounds or for the treatment of materials containing polyamide.

In particular, it could be of value within the framework of regenerating the starting materials of polyamide polymers.

The Examples which follow provide an illustration of the characteristics, variants and advantages of the present invention without however limiting its scope

DESCRIPTION OF THE ATTACHED FIGURES

The sequence listing is established according to WIPO standard ST 23 and comprises:

SEQ ID NO: 1: amino acid sequence corresponding to the enzyme PAM II according to the invention, SEQ ID NO 2: DNA (pam II) coding for the amidase PAM II, SEQ ID NO: 3: amino acid sequence corresponding to PAM I, SEQ ID NO: 4: DNA coding for the enzyme PAM I.

EXAMPLES

Figure 1:
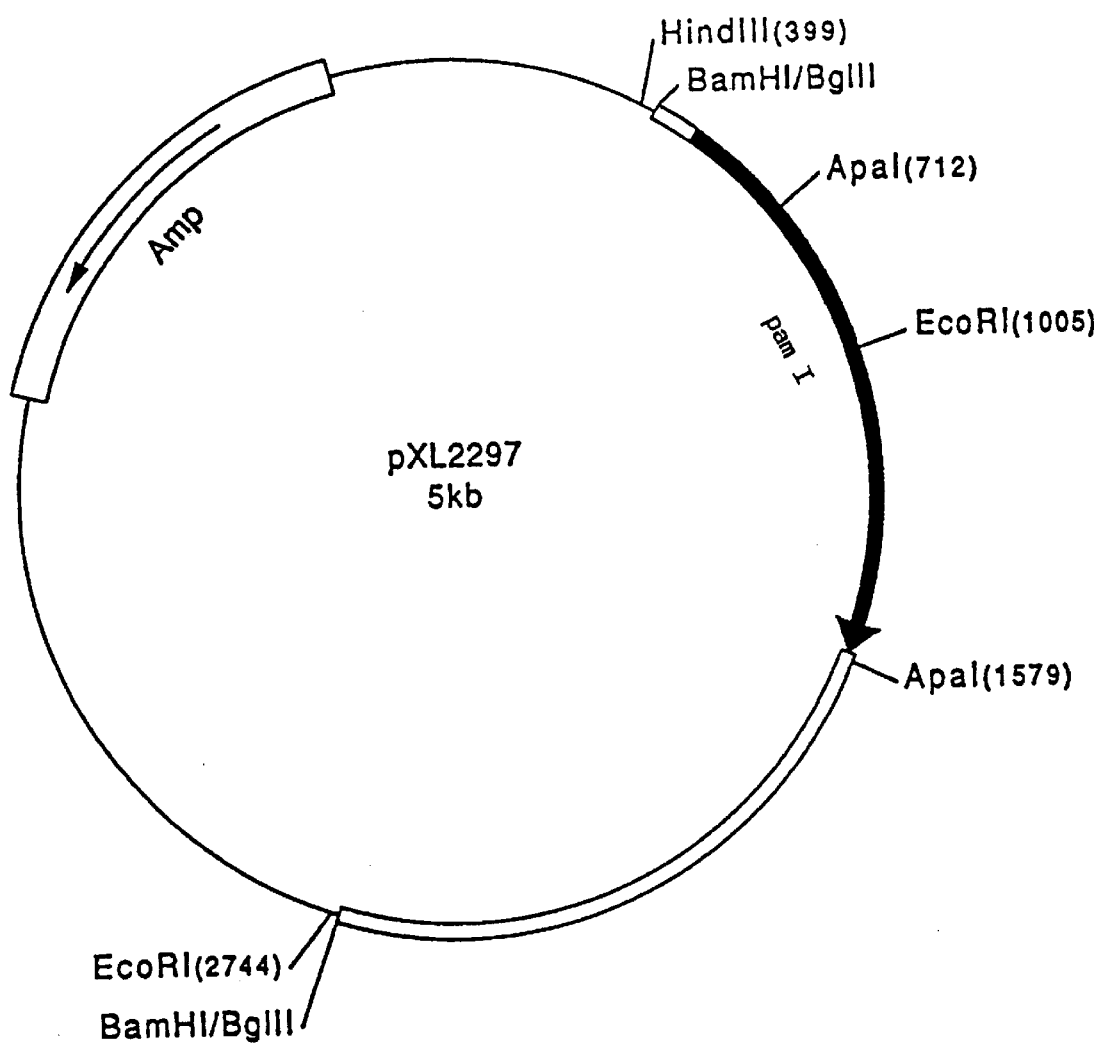
FIG. 1 shows the restriction map of plasmid pXL2297 containing the gene (pam I) coding for the amidase PAM I.

EXAMPLE 1: ISOLATION AND IDENTIFICATION OF THE WILD-TYPE STRAIN COMAMONAS ACIDOVORANS N 12

1.1 MICROBIOLOGICAL SCREENING

A vast microbiological screening operation enabled the strain *Comamonas acidovorans* N 12 to be selected from various biotopes.

1.2 SELECTION-IDENTIFICATION OF THIS MICROORGANISM:

This microorganism was selected with the aid of an amidase activity test on synthetic oligomers of PA 6.6. The evaluation of activity will be given in detail below.

The selected microorganism was then identified on the basis of its morphological, physiological, biochemical and possibly antigenic properties, in completely traditional manner, by the Bacteriology Laboratory of the INSTITUT PASTEUR.

On the basis of these results and the hydrolytic activities on a mixture of oligomers AB, ABA, BAB and ABAB, the natural strain selected was then subjected to a more thorough characterization.

EXAMPLE 2: THOROUGH CHARACTERIZATION OF COMAMONAS ACIDOVORANS N 12

2.1 OPTIMIZATION OF THE CULTURE CONDITIONS:

The optimum culture medium is M9YE3 having the following composition:

| | |
|---|---|
| $KH_2PO_4$ | 0.75 g/l |
| $K_2HPO_4 \cdot 3H_2O$ | 1.00 g/l |
| $Na_2HPO_4 \cdot 12H_2O$ | 1.00 g/l |
| $(NH_4)_2SO_4$ | 2.50 g/l |
| Yeast extract | 3.00 g/l |
| $MgSO_4 \cdot 7H_2O$ | 1.00 g/l |
| $FeSO_4 \cdot 7H_2O$ | 2.30 mg/l |
| $MnSO_4 \cdot 7H_2O$ | 2.70 mg/l |
| $CoCl_2 \cdot 2H_2O$ | 2.30 mg/l |
| $CaCl_2 \cdot 2H_2O$ | 1.50 mg/l |
| $CuSO_4 \cdot 5H_2O$ | 0.25 mg/l |
| pH | 7.2 | and supplemented with 10 g/l of adipic acid salt.

The cultures are prepared in Erlenmeyer flasks filled to ⅕ of their total volume. The media are incubated at 30° C. and stirred at 150 rpm.

The preculture is composed of 10 ml of LB medium:

| | |
|---|---|
| Tryptone | 10 g/l |
| Yeast extract | 5 g/l |
| NaCl | 10 g/l | inoculated with a colony originating from a Petri dish containing M9YE3 agar medium and 5 g/l of a compound containing an amide group, such as pentameric to decameric oligomers of PA 6.6.

The culture is then inoculated at 1% with the optimum medium (v/v). When culture is complete, the cell production is determined via a dry extract obtained by the drying, overnight at 105° C., of a cell residue obtained after centrifugation (10 min at 12,000 g)

To obtain maximum efficacy in the hydrolysis, a compound containing at least one amide group is advantageously introduced into the medium.

According to another preferred characteristic of the invention, the carbon source contains, together with the soluble components, a complement advantageously selected from carbohydrates, sucrose being particularly preferred.

To obtain maximum efficacy in the hydrolysis, a compound containing at least one amide group is advantageously introduced into the medium.

2.2 ENZYMATIC HYDROLYSIS—MEASUREMENT OF ACTIVITY OF THE WILD-TYPE MICROORGANISM:

The activity is measured at 28° C. in a 10.5 mmol/l phosphate buffer at pH 7.5 and with a final volume of 1 ml.

TABLE 1 below gives the results obtained.

TABLE 1

| SUBSTRATE (concentration in the test in g/l) | *Comamonas acidovorans* N 12 |
|---|---|
| (1.4) AB → A + B | 280 mg of A/h.g of dry cells |
| (2.6) ABA → AB + A | 215 mg of AB/h.g of dry cells |
| (1.4) ABAB → BAB + A | 410 mg of BAB/h.g of dry cells |

EXAMPLE 3: PURIFICATION OF THE POLYAMIDE HYDROLASE OF *COMAMONAS ACIDOVORANS* N 12 ACCORDING TO THE INVENTION

Standard protocol:

The activity of this enzyme (PAM II) is monitored by determining the activity in the hydrolysis of ABAB to BAB+A.

3.1 GLOSSARY:

| | |
|---|---|
| DTE = | 1,4-dithioerythritol |
| EDTA acid = | ethylenediaminetetraacetic |
| CHAPS = | 3-[(3-cholamidopropyl)dimethylammonio]-propane-1-sulfonate |
| SDS = | sodium dodecylsulfate |

3.2 PREPARATION OF THE ENZYMATIC EXTRACTS:

The starting material consists of cells originating from a 20-hour culture in a 2.5 l flask filled with 500 ml of M9YE3 medium described in Example 2, supplemented with 10 g/l of adipic acid salt.

FIRST EXTRACTION BY ULTRASONIC TREATMENT:

25 g of *Comamonas acidovorans* cells are resuspended in 75 ml of 100 mM Tris-HCl buffer, pH 7.5, containing 1 mM DTE, 5 mM EDTA, 100 mM KCl and 15% v/v of glycerol.

The suspension is then subjected to a discontinuous ultrasonic treatment (10% treatment, 90% rest) in melting ice for 70 min.

The suspension is then centrifuged for 1 h 30 min at 50,000 g (Beckman ultracentrifuge).

This finally gives:
→ on the one hand 90 ml of supernatant (S1) containing 21 mg/ml of proteins, i.e. 1890 mg of proteins of specific activity 6 μmol/h/mg (11,340 units in total); and
→ on the other hand a residue (C1), which is resuspended in 30 ml of 25 mM Tris-HCl buffer, pH 8, containing 2 mM DTE, 8 mM CHAPS and 15% v/v of glycerol.

It is this residue, also containing polyamidase II activity, which is subsequently treated. It is pointed out that it is possible, after the removal of salt from the 90 ml of supernatant in the same buffer without glycerol, and renewed ultracentrifugation, to purify and reconcentrate into a new, very fine residue the polyamidase II activity which is apparently soluble in the first centrifugation. In fact, reducing the density of the buffer (by removing the glycerol) accelerates the precipitation of the very fine particles. This information is consistent with the fact that the first supernatant cannot be isolated by chromatography, for example on a MonoQ column, since the activity is found throughout the gradient.

COMPLEMENTARY TREATMENT OF THE RESIDUE FROM THE FIRST CENTRIFUGATION:

The resuspended residue (C1) is centrifuged for 30 min at 4000 g in order to precipitate the cells not lyzed by the first ultrasonic treatment.

The supernatant (S2) is then collected and subjected to a discontinuous ultrasonic treatment (10% treatment, 90% rest) in melting ice for 20 min. It is then centrifuged again for 2 h at 50,000 g and the supernatant (S3) is collected.

PURIFICATION STEPS BY CHROMATOGRAPHY:

1st step: The supernatant S3 is chromatographed in three portions on a MonoQ HR 10/10 column (Pharmacia) equilibrated in 25 mM Tris-HCl buffer, pH 8, containing 2 mM DTE, 8 mM CHAPS and 15% v/v of glycerol. Elution is carried out with a linear gradient from 0 to 0.6M NaCl over 60 min at a rate of 3 ml/min. The polyamidase II activity is eluted at about 0.2M NaCl as a fairly broad peak. The active fractions are pooled and concentrated to 5 ml on a Centriprep 10 (Amicon).

2nd step: 5 ml of 25 mM Tris-HCl buffer, pH 8, containing 1 mM DTE, 8 mM CHAPS, 1.5M ammonium sulfate and 15% v/v of glycerol, are added to the 5 ml collected above. These 10 ml are then chromatographed in two portions on a Phenylsuperose HR 10/10 column (Pharmacia) equilibrated in 25 mM Tris-HCl buffer, pH 8, containing 2 mM DTE, 8 mM CHAPS, 1 M ammonium sulfate and 15% v/v of glycerol. Elution is carried out with a linear gradient from 1 to 0M ammonium sulfate over 70 min at a rate of 1.25 ml/min. The polyamidase activity is eluted at about 0.8M ammonium sulfate. The active fractions are pooled and concentrated to 400 μl on a Centriprep 10 (Amicon).

3rd step: The above 400 μl are chromatographed in two portions on a TSK G3000 SW column (Supelco) equilibrated in 100 mM Tris-HCl buffer, pH 7.5, containing 2 mM DTE, 8 mM CHAPS, 150 mM NaCl and 15% v/v of glycerol, and eluted at 0.5 ml/min. The activity is found from exclusion up to a molecular weight of about 30 kDa. The most active fractions are pooled and made up to a volume of 5 ml and the salt is removed on PD10 Sephadex G25 columns (Pharmacia) (2.5 ml per column) equilibrated and eluted in 25 mM Tris-HCl buffer, pH 8, containing 2 mM DTE, 8 MM CHAPS and 15% v/v of glycerol.

4th step: The 7 ml resulting from the removal of salt on PD10 are chromatographed on a MonoQ HR 5/5 column (Pharmacia) equilibrated in 25 mM Tris-HCl buffer, pH 8, containing 2 mM DTE, 8 mM CHAPS and 15% v/v of glycerol. Elution is carried out with a linear gradient from 0 to 0.6M NaCl over 30 min at a rate of 1 ml/min. The polyamidase activity is eluted at about 0.15M NaCl as a fairly broad peak. The active fractions are pooled and, after the addition of 0.05% of SDS, are concentrated to 200 μl on a Centriprep 10 and then a Centricon 10 (Amicon).

5th step: The 200 μl collected are injected onto a TSK G3000 SW column equilibrated in 40 mM sodium sulfate, 20 mM sodium phosphate buffer, pH 6.8, containing 0.25% w/v of SDS, and eluted at a rate of 0.25 ml/min. The polyamidase emerges as a narrow peak, which is monitored by electrophoresis. This material is used for sequencing.

DETERMINATION OF THE MOLECULAR WEIGHT BY ELECTROPHORESIS:

The molecular weight, determined by polyacrylamide gel electrophoresis, varies according to the method of preparing the polyamidase II sample.

In the presence of 2.5% of SDS and 5% of mercaptoethanol, a band is found between 36 and 40 kDa but, if heated for 5 min at 90° C., the same sample now only migrates to a molecular weight of about 150 kDa. According to its purification protocol, this phenomenon is characteristic of some proteins associated with membranes.

SEQUENCING:

A batch of about 60 μg of polyamidase, prepared by the standard protocol but starting from 60 g of cells and replacing the Phenylsuperose step with a second MonoQ HR 10/10 step, is digested directly with 5 μg of the enzyme LysC in the presence of 0.25% w/v of SDS. The fragments obtained were purified on a Vydac C18 column.

The sequence SEQ ID NO: 1 was obtained using conventional nucleotide sequencing techniques.

EXAMPLE 4: ENZYMATIC HYDROLYSIS OF OLIGOMERS FORMED BY MONOMERS A AND B JOINED TOGETHER BY SECONDARY AMIDE LINKAGES, WITH THE AID OF A MIXTURE OF ENZYMES ACCORDING TO THE INVENTION AND PAM I HYDROLASE

Instead of the pure enzymes, the present Example utilizes their biological precursors, namely the strain *Comamonas acidovorans* N 12 according to the invention and a strain accommodating the pam I gene (SEQ ID NO: 4 attached) and producing the, enzyme PAM 1 (SEQ ID NO : 3 attached), said strain being constructed according to the protocol given below.

The aim of this construction is to obtain the pam I gene (coding for the enzyme-PAM I), which is preceded by the ribosome binding site of the phage λ cII gene and which is expressed from the *E. coli* tryptophan operon promoter. To do this, an NdeI restriction site was created at the pam I initiation codon by the PCR technique using, as template, plasmid pXL2297 (FIG. 1) accommodated by the strain I 1495 deposited in the CNCM on Nov. 29, 1994. The 208 bp NdeI-ApaI fragment containing the 5' end of the pam I gene was amplified by PCR, care being taken to introduce a HindIII site upstream of the NdeI site by means of the pair of nucleotide primers (5'-AGCAAGCTTGGAGGCCATATGAATAC GAC-3') and (5'-CACCGGTGGGCCCCTC-3'). The amplified HindIII-ApaI fragment was cloned into pUC29 (Benes et al. (1993), Gene 130: 151–152) digested by HindIII and ApaI, and the pam I gene was reconstituted by introducing the 867 bp ApaI fragment of pXL2297 at the ApaI site. An NcoI site is thus located about thirty nucleotides downstream of the pam I stop codon. The adjacent 500 bp NdeI-EcoRI and 600 bp EcoRI-NcoI fragments of this plasmid were inserted into pXL2158 (patent FR 92-09 882) digested at the NdeI site located immediately downstream of the tryptophan promoter.

Figure 2:
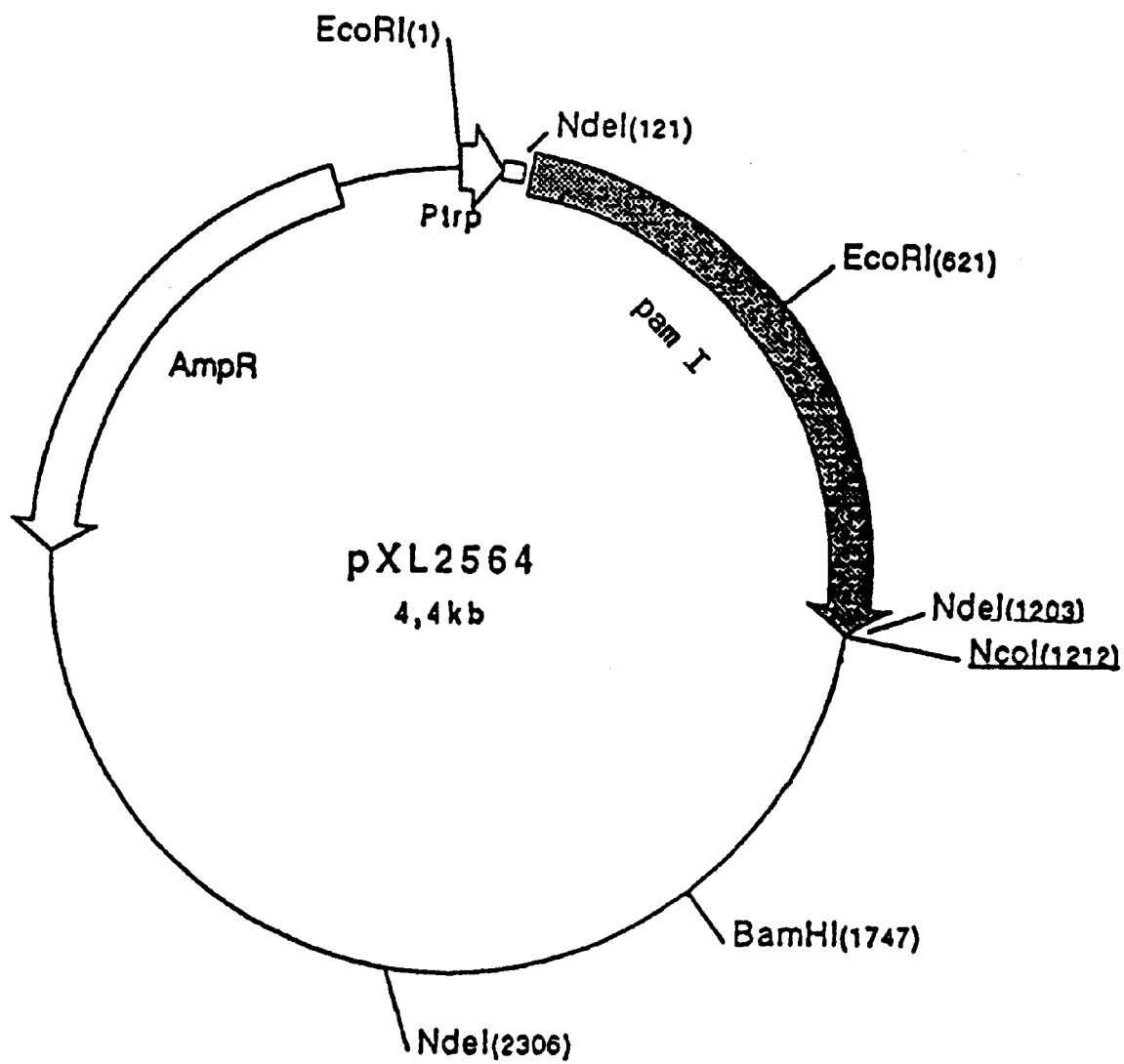
FIG. 2 shows the restriction map of plasmid pXL2564 containing the gene (pam I) coding for PAM I.

Thus plasmid pXL2564 (described in FIG. 2) is a derivative of pBR322 (Sucliffe (1978), Nucleic Acid Res. 5 : 2721) containing a gene conferring ampicillin resistance and the pam I gene under the control of the Ptrp-RBScII expression cassette.

Plasmid pXL2564 was introduced into the *E. coli* strain TG1, the microorganisms being selected on ampicillin LB. A clone containing pXL2564 (called strain PAM I) was transferred twice onto agar dishes and cultured at 37° C. in M9 glucose medium containing 100 µg/ml of ampicillin, according to the procedure described in patent FR 2 694 571.

The strain *Comamonas acidovorans* N 12 was cultivated for 19 hours under the same conditions as those described in section 2.1 above.

A batch of oligomers was used which consisted of monomers A=adipic acid and B=hexamethylenediamine (HMD) and had a mean $DP_n$ of 4.

25.25 g of oligomers with a mean $DP_n$ of 8 are resuspended in 300 ml of water. 200 ml of water containing the cells (i.e. 3.1 g in total) are added. The whole is stirred for 18 hours under a stream of nitrogen.

The solution is centrifuged and the supernatant (400 ml) is recovered. A dry weight of 14 g/l is measured on the supernatant. A fraction is taken for analysis of the oligomers of adipic acid and HMD.

The results of this analysis are presented in Table 2 below.

TABLE 2

| COMPOUND | CONTENT DETERMINED (g/l) |
|---|---|
| HMD | 13.8 |
| ADIPIC ACID | 20 |
| AB | 1 |
| BAB | 3.6 |
| ABA | 0.7 |
| ABAB | 0.3 |

The molar yield of adipic acid monomer formed is 66% and the molar yield of HMD is 58%.

The molar yield of monomers and oligomers with a DP of less than 4, expressed in mol of monomers, is 72%.

What is claimed is:

1. An isolated or substantially purified enzyme with amidase activity, which is a native Comamonas bacterium enzyme with amidase activity or an enzyme expressed by a recombinant bacterium comprising a DNA sequence encoding a native Comamonas bacterium enzyme with amidase activity, said enzyme being active with respect to (poly) amide substrates having the following formula (I):

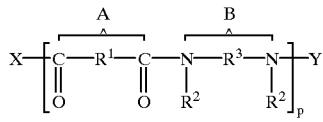

(I)

in which:

A and B are monomer units, $R^1$ and $R^3$ are identical or different divalent radicals representing a substituted or unsubstituted, linear or branched (cyclo)alkylene, an arylene, or an arylalkylene, the aromatic radicals optionally being polycondensates and the number of carbons in the alkylenes being greater than or equal to 4, $R^2$ corresponds to identical or different radicals selected from hydrogen and alkyl radicals having from 1 to 6 carbons, X is
either $X^1$ is OH, OM or $OR^4$, where M is selected from metals, and $R^4$ is a linear or branched alkyl comprising from 1 to 6 carbon atoms,
or $X^2$ is

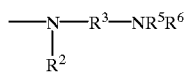

where $R^2$ and $R^3$ are as defined above and $R^5$ and $R^6$, which are identical or different, have the same definition as that given above for $R^2$, Y is:
either $Y^1$ is hydrogen,
or $Y^2$ is

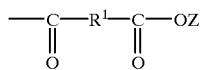

where $R^1$ is as defined above and Z is hydrogen, $M^1$ defined in the same way as M, or $R^4$, wherein
if X is $X^1$, then Y is $Y^1$ or $Y^2$, or,
if X is $X^2$, then Y is $Y^2$,
and p is between 1 and 4;
and it is capable of converting said substrate (I) to monomers A and monomers B.

2. The isolated or substantially purified enzyme with amidase activity, according to claim 1, comprising the peptide sequence as shown in SEQ ID NO: 1.

3. The isolated or substantially purified enzyme according to claim 1, which is capable of hydrolyzing substrate (I) containing at least one carboxyl end group.

4. The isolated or substantially purified enzyme according to claim 1, wherein:
it is active towards a substrate (I) formed by a tetramer of the type ABAB,
and it is capable of converting this substrate to a trimer ABA+A with a specific enzymatic activity ($U_s$)—expressed in $\mu$mol of hydrolyzed $ABAB \times h^{-1} \times mg^{-1}$—of greater than or equal to 1000.

5. An isolated or substantially purified enzyme according to claim 1, wherein:
it is active towards a substrate (I) formed by a trimer ABA,
and it is capable of converting this trimer to a dimer AB and a monomer A with a specific enzymatic activity ($U_s$)—expressed in $\mu$mol of hydrolyzed AB/h/mg of enzyme—of greater than or equal to 1000.

6. An isolated or substantially purified enzyme according to claim 1, wherein:
it is active towards a substrate (I) formed by a dimer of the type AB,
and it is capable of converting this dimer to two monomers A and B with a specific enzymatic activity ($U_s$)—expressed in $\mu$mol of hydrolyzed AB/h/mg of enzyme—of greater than or equal to 1500.

7. An isolated or substantially purified enzyme according to claim 1, wherein it is produced by microorganisms of the *Comamonas acidovorans* (N 12) type or of the same type as the strain referenced and deposited in the Collection Nationale de Cultures de Micro-organismes under no. I 1522 on Jan. 4, 1995, and/or by their recombinant microorganisms.

8. An isolated or substantially purified enzyme with amidase activity, which is a native Comamonas bacterium enzyme with amidase activity or an enzyme expressed by a recombinant bacterium comprising a DNA sequence encoding a native Comamonas bacterium enzyme with amidase activity, said enzyme being active with respect to (poly) amide substrates having the following formula (II):

(II)

$$U-\left[\underset{\overset{\|}{O}}{\overset{a}{C}}-R^3-\underset{\overset{|}{R^2}}{\overset{b}{N}}\right]_q-V$$

in which:
  a, b and c are monomer units,
  $R^2$ corresponds to identical or different radicals selected from hydrogen and alkyl radicals having from 1 to 6 carbons, and $R^3$ is identical or different divalent radicals representing a substituted or unsubstituted, linear or branched (cyclo)alkylene, an arylene, or an arylalkylene, the aromatic radicals optionally being polycondensates and the number of carbons in the alkylenes being greater than or equal to 4,
  U is OH, OM or $OR^4$, where M is selected from metals, and $R^4$ is a linear or branched alkyl comprising from 1 to 6 carbons, and V is hydrogen,
  and q is between 1 and 8.

9. The isolated or substantially purified enzyme according to claim 8, which is capable of hydrolyzing substrate (II) containing at least one carboxyl end group.

10. An isolated DNA fragment containing a DNA sequence coding for an enzyme with amidase activity, which is selected from the sequences of:
  the DNA sequence as represented by SEQ ID NO: 2 and coding for at least one enzyme with amidase activity, and
  an analog of this sequence which results from the degeneracy of the genetic code.

11. An isolated or substantially purified enzyme produced by the expression of the DNA sequence according to claim 10.

12. A microorganism comprising at least one expression cassette comprising the DNA sequence according to claim 10 and optionally, upstream thereof, at least one promoter sequence and at least one ribosome binding site.

13. A process for the hydrolysis of (poly)amides, comprising conducting enzymatic hydrolysis on substrates comprising (poly)amides of the following formula (I):

(I)

$$X-\left[\overset{A}{\overbrace{\underset{\overset{\|}{O}}{C}-R^1-\underset{\overset{\|}{O}}{C}}}-\overset{B}{\overbrace{\underset{\overset{|}{R^2}}{N}-R^3-\underset{\overset{|}{R^2}}{N}}}\right]_p-Y$$

in which:
  A and B are monomer units,
  $R^1$ and $R^3$ are identical or different divalent radicals representing a substituted or unsubstituted, linear or branched (cyclo)alkylene, an arylene, or an arylalkylene, the aromatic radicals optionally being polycondensates and the number of carbons in the alkylenes being greater than or equal to 4,
  $R^2$ corresponds to identical or different radicals selected from hydrogen and/or alkyl radicals advantageously having from 1 to 6 carbons,
  X is:
    either $X^1$ is OH, OM or $OR^4$, where M is selected from metals, and $R^4$ is a linear or branched alkyl comprising from 1 to 6 carbon atoms,
    or $X^2$ is $$-\underset{\overset{|}{R^2}}{N}-R^3-NR^5R^6$$

where $R^2$ and $R^3$ are as defined above and $R^5$ and $R^6$, which are identical or different, have the same definition as that given above for $R^2$, Y is:
  either $Y^1$ is hydrogen,
  or $Y^2$ is $$-\underset{\overset{\|}{O}}{C}-R^1-\underset{\overset{\|}{O}}{C}-OZ$$

where $R^1$ is as defined above and Z is either hydrogen, $M^1$ defined in the same way as M, above, or $R^4$ as defined above, wherein
    if X is $X^1$, then Y is $Y^1$ or $Y^2$, or,
    if X is $X^2$, then Y is $Y^2$,
  and p is between 1 and 4;
  and obtaining monomers A and B.

14. The process of claim 1, wherein said amidase enzyme is a native Comamonas bacterium enzyme with amidase activity or an enzyme expressed by a recombinant bacterium comprising a DNA sequence encoding a native Comamonas bacterium enzyme with amidase activity, said enzyme being active with respect to (poly)amide substrates having formula (I).

15. The process of claim 1, wherein said amidase enzyme has the amino acid sequence encoded by the nucleic acid of SEQ ID NO:2.

16. A process for hydrolysis of substrates comprising oligomers whose degree of polymerization ($DP_n$) is less than 40, which oligomers are derived from polyamides resulting from polycondensation of between diacid monomers (A) and diamine monomers said process produces one or more of monomers A, monomers B, and oligomers with a $DP_n$ less than or equal to 3, and, wherein said process utilizes at least one enzyme according to claim 1, as well as at least one other enzyme, said at least one other enzyme selected from the group consisting of:
    the enzyme E3 produced either in its wild-type form or biological precursor thereof, or as a product of recombinant expression or biological precursor thereof of the nyl-c gene of Flavobacterium so. K 172, and,
    the enzyme PAM I as defined by the amino acid sequence of SEQ ID NO:3 or the enzyme produced under the control of the microorganism referenced and deposited in the Collection Nationale de Cultures de Microolganismes—Institut Pasteur PARIS—under No. I 1495 on Nov. 29, 1994, either in its wild-type form or biological precursor, or as a product of recombinant expression or biological precursor.

17. A process for the hydrolysis of substrates at least partly formed by substrate (I) as defined, wherein said process comprises using at least one enzyme according to claim 1.

18. A process for the hydrolysis of substrates at least partly formed by substrate (II) as defined in claim 4, wherein said process comprises using an enzyme according to claim 4.

19. The process of claim 18, wherein substrate (II) is partially hydrolyzed.

20. The process of claim 18, wherein the hydrolysis of substrate (II) includes at least one other enzyme.

* * * * *